United States Patent
Ellis et al.

(10) Patent No.: US 10,842,469 B2
(45) Date of Patent: Nov. 24, 2020

(54) BIOPSY TRACKING SYSTEMS AND METHODS

(71) Applicant: UNIVERSITY HOSPITALS OF CLEVELAND, Cleveland, OH (US)

(72) Inventors: Rodney Ellis, Pepper Pike, OH (US); Deborah A. Kaminsky, Cleveland Heights, OH (US)

(73) Assignee: UNIVERSITY HOSPITALS OF CLEVELAND, Cleveland, OH (US)

( * ) Notice: Subject to any disclaimer, the term of this patent is extended or adjusted under 35 U.S.C. 154(b) by 227 days.

(21) Appl. No.: 15/317,258

(22) PCT Filed: Jun. 9, 2015

(86) PCT No.: PCT/US2015/034806
§ 371 (c)(1),
(2) Date: Dec. 8, 2016

(87) PCT Pub. No.: WO2015/191514
PCT Pub. Date: Dec. 17, 2015

(65) Prior Publication Data
US 2017/0105709 A1    Apr. 20, 2017

Related U.S. Application Data

(60) Provisional application No. 62/010,255, filed on Jun. 10, 2014.

(51) Int. Cl.
*A61B 10/02* (2006.01)
*A61B 10/00* (2006.01)
(Continued)

(52) U.S. Cl.
CPC ........ *A61B 10/0096* (2013.01); *A61B 5/0035* (2013.01); *A61B 5/0059* (2013.01);
(Continued)

(58) Field of Classification Search
CPC ......... A61B 10/00; A61B 10/025; A61B 5/05; A61B 6/00; A61B 90/36; A61B 10/0096;
(Continued)

(56) References Cited

U.S. PATENT DOCUMENTS

| 4,793,363 A | 12/1988 | Ausherman et al. |
| 2006/0258933 A1 | 11/2006 | Ellis et al. |

(Continued)

FOREIGN PATENT DOCUMENTS

WO    WO 2007/079197 A2    7/2007

OTHER PUBLICATIONS

International Search Report for PCT Patent Application PCT/US2015/034806 dated Sep. 14, 2015.

*Primary Examiner* — Carl H Layno
*Assistant Examiner* — Jon Eric C Morales
(74) *Attorney, Agent, or Firm* — Fay Sharpe LLP

(57) ABSTRACT

A biopsy tracking kit includes a trocar, a stylet, a biopsy needle, a biopsy tracking cassette, and a fiducial marker. The trocar has a cannula with a blunt first end and a second end with a cup. The stylet has a conical tip at a first end and a cap on a second end that engages the cup of the trocar and prevents the stylet from falling through the trocar. The biopsy needle is used to obtain biopsy specimens when inserted through the trocar. The biopsy tracking cassette comprises an internal surface with a plurality of coded zones in a single column, and is used to differentiate the biopsy specimen into smaller regions. The fiducial marker is oriented to mark the position where the biopsy specimen was taken. Other systems, devices, and methods of use are also described.

22 Claims, 6 Drawing Sheets

(51) Int. Cl.

| | | |
|---|---|---|
| G01N 1/00 | (2006.01) | |
| A61B 90/92 | (2016.01) | |
| A61B 5/00 | (2006.01) | |
| A61B 5/055 | (2006.01) | |
| A61B 6/03 | (2006.01) | |
| A61B 8/08 | (2006.01) | |
| A61B 18/02 | (2006.01) | |
| A61B 18/04 | (2006.01) | |
| A61M 25/01 | (2006.01) | |
| A61M 25/06 | (2006.01) | |
| A61N 5/06 | (2006.01) | |
| A61N 5/10 | (2006.01) | |
| A61N 7/02 | (2006.01) | |
| A61B 90/00 | (2016.01) | |
| A61B 17/34 | (2006.01) | |

(52) U.S. Cl.
CPC ............ *A61B 5/055* (2013.01); *A61B 5/4839* (2013.01); *A61B 6/032* (2013.01); *A61B 6/037* (2013.01); *A61B 8/481* (2013.01); *A61B 10/0233* (2013.01); *A61B 18/02* (2013.01); *A61B 18/04* (2013.01); *A61B 90/92* (2016.02); *A61M 25/0102* (2013.01); *A61M 25/0662* (2013.01); *A61N 5/062* (2013.01); *A61N 5/1001* (2013.01); *A61N 5/1045* (2013.01); *A61N 5/1077* (2013.01); *A61N 7/02* (2013.01); *G01N 1/00* (2013.01); *A61B 2010/0225* (2013.01); *A61B 2017/3456* (2013.01); *A61B 2090/3908* (2016.02); *A61B 2090/3925* (2016.02); *A61B 2090/3937* (2016.02); *A61B 2090/3954* (2016.02); *A61B 2090/3966* (2016.02); *A61B 2090/3995* (2016.02); *G01N 2001/005* (2013.01); *G01N 2001/007* (2013.01)

(58) Field of Classification Search
CPC ......... A61N 5/103; B01L 3/00; B01L 3/5085; C12M 45/22; G01N 1/31; G01N 1/36
USPC .................................................. 600/567, 407
See application file for complete search history.

(56) References Cited

U.S. PATENT DOCUMENTS

| | | |
|---|---|---|
| 2007/0116612 A1 | 5/2007 | Williamson, IV |
| 2008/0146964 A1 | 6/2008 | Hoffman et al. |
| 2011/0015542 A1 | 1/2011 | Hibner et al. |

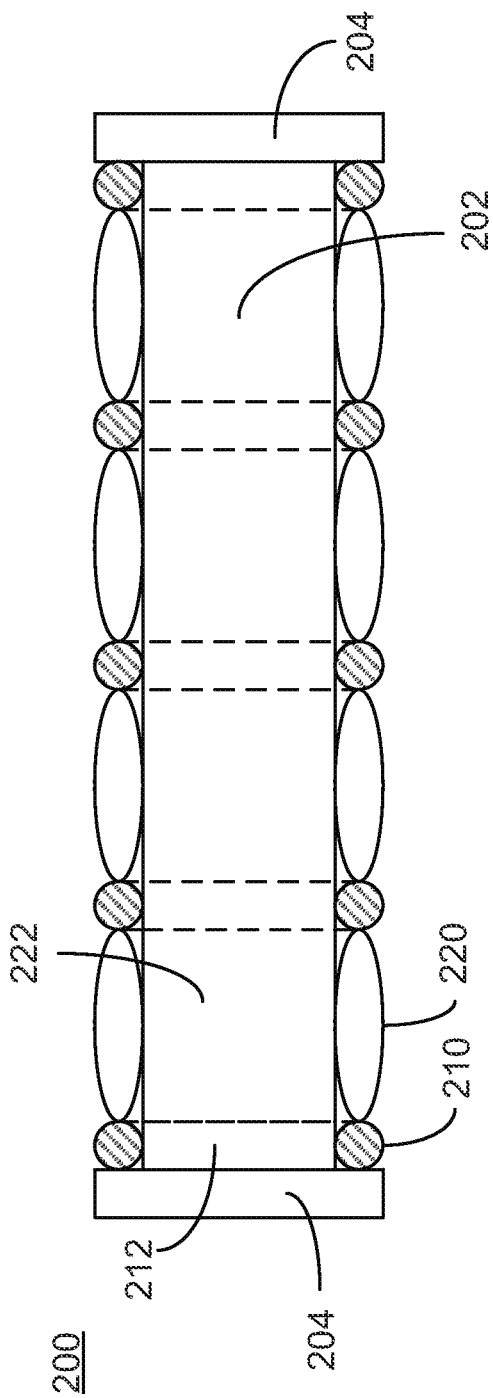
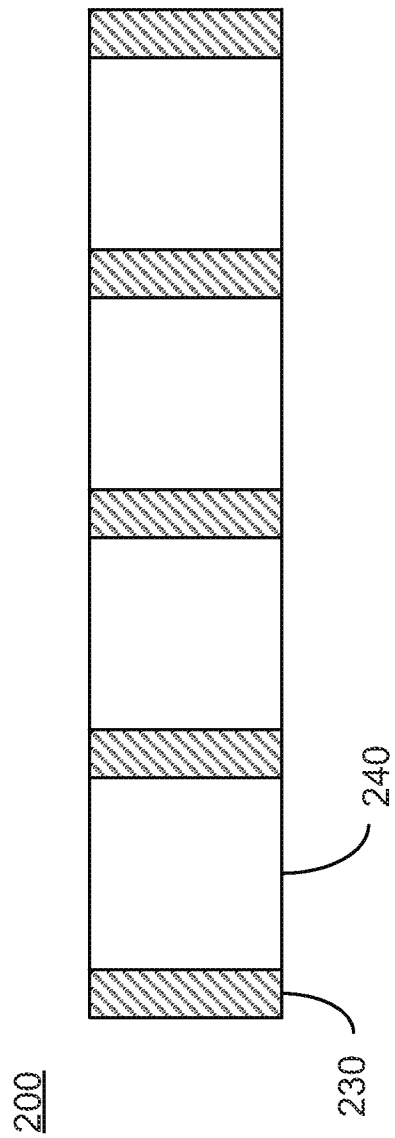

BIOPSY TRACKING SYSTEMS AND METHODS

CROSS-REFERENCE TO RELATED APPLICATIONS

This application is a 371 of PCT Application Serial No. PCT/US2015/034806, filed Jun. 9, 2015, which claims priority to U.S. Provisional Patent Application Ser. No. 62/010,255, filed on Jun. 14, 2014, which is fully incorporated by reference.

BACKGROUND

The present disclosure relates to tracking systems, methods, apparatuses, and devices for performing biopsies and for particularly recording the site from which a biopsy tissue "core" was acquired such that the results of such core analysis can be correlated to the in-vivo location for use in subsequent medical procedures and subsequent localized modulated medical treatment/s. The systems include a biopsy tracking kit using a trocar and stylet to access a targeted tissue from a living organ from which a columnar biopsy specimen is taken. A corresponding physical fiducial marker is then inserted at the biopsy site, or the biopsy site is tracked using a "virtual" approximation of the in-situ location, such as during an image-guided biopsy procedure using a biopsy needle tip. The columnar biopsy specimen is subsequently differentiated into different regions so that the data reported for the biopsy specimen may be correlated to a more specific location within the biopsy site. For example, known non-diseased regions, and diseased locations, in addition to the severity or aggressiveness of disease may be noted as represented by for example tumor markers and tissue staining. The location of abnormal but non-diseased tissue sites may also be useful for subsequent patient interventions and surveillance. As such, any information reported through a pathology analysis can be linked to a given region, be used to identify a localized area in the tissue/organ, and mark that localized area as one that should be treated, not treated, treated with higher intensity, or with lower intensity when treatment related toxicity is desired. This allows treatment to be specifically focused and personalized to a particular patient's own disease status and provides a record of normal and diseased areas that may be used to inform subsequent medical interventions, to improve clinical outcomes and patient management decisions, and potentially reduce treatment related side effects and overall treatment costs.

Biopsies are taken of tissues of patients to analyze the tissues in a specialized laboratory for disease such as cancer. For example, to biopsy the prostate, a cutting device can be inserted through the rectum of the patient to a position adjacent to the prostate, thus aligning such a needle for access to the prostate. The biopsy needle "gun" has a biopsy needle attached with a firing mechanism that will trap tissue for removal. Such a cutting device is then removed and a biopsy tissue specimen or "core" of the prostate is taken for histopathology analysis. Thus, biopsy specimens are placed in tissue cassettes and labeled with identifying information. Biopsy specimens are very long and thin, and can be easily broken into smaller fragments during transport. The specimens are then fixed and examined.

Standard treatment for prostate cancer generally has been directed at the entire organ Traditionally, organ-targeted prostate cancer treatments have been accomplished either by surgical resection of the entire gland or perhaps by treating the entire prostate by directing multiple beams of radiation or thermal therapies into the pelvis to encompass the entire gland in a uniform dose. More recently, radiation therapy and other treatments such as thermal therapies (e.g. cryotherapy) have incorporated whole gland uniform treatment. Radiation and thermal treatments for such generalized whole gland treatments often have the impact of over-exposing normal radiosensitive tissues to unnecessary treatment, thereby increasing the likelihood of treatment related morbidities. Such poorly directed curative therapies lead to increased cost of care and decreased patient quality of life when therapies cause harm to normal structures such as the neurovascular bundle, urethra, or rectum, and result in treatment-related toxicities such as impotence, incontinence or rectal fissure that must be medically managed for the remaining life of the cancer survivor.

Alternate thermal methods such as cryotherapy have also been explored, though again generally directed to treat, or freeze, the entire organ. While newer focal cryotherapy methods attempt to more uniquely focus the freezing process to a section of the gland in order to decrease the incidence of treatment related morbidity, appropriate targeting methods continue to rely on general assumptions about the location of areas of high tumor burden. Other alternative methods include applications of high frequency ultrasound (HIFU) and laser therapies.

As computers have become better at assisting in treatment planning, it has become standard to use three dimensional (3-D) treatment planning to shape the individual field for radiation therapy to treat, for example, only the prostate itself, commonly adding a margin beyond the outline of the target gland of about 5 to 15 millimeters beyond the edge of the gland. Use of this planning convention allows for higher confidence that the entire target tissue (e.g. the entire prostate gland) will receive an adequate dose to achieve curative intent. Clinical trials have confirmed that using higher doses of radiation is associated with higher cure rates. Higher doses however are associated with higher rates of treatment related toxicities.

An alternative method for achieving a high dose delivered to the entire gland is known as brachytherapy, or the placement of either temporary High Dose Rate (HDR) or permanent Low Dose Rate (LDR) radioactive sources within the prostate. In these procedures, the 3-D treatment planning used for the image guided procedure applies a treatment margin beyond the prostate in the range of 1-10 mm.

A gross target volume (GTV) of a treatment target may be defined by anatomic image studies, which may then be used to further define a clinical target volume (CTV), typically comprising the GTV plus an adequate margin to account for microscopic disease at the edge of the GTV and allowance for motion of the GTV from patient positioning variation during image study. In Brachytherapy, the margin for treatment planning (PTV) may be reduced beyond the GTV as there is no motion of the organ that does not include the sources, and daily set-up errors can be eliminated. A biological target volume (BTV) typically represents a region defined by a functional study that may be completely within the GTV, or may expand the GTV by showing disease extending beyond the margins defined by the GTV on the anatomic study. The use of BTV allows for dose modulation to apply increased therapeutic intensity to a BTV suggested by imaging.

A newer external beam radiation therapy technique, referred to as Intensity Modulated Radiation Therapy or IMRT, has become available for treating the entire organ with tighter margins of as little as 4 millimeters. IMRT provides options for targeting small volume (<1 cc) regions within a treatment planning volume (PTV) to focus higher doses than the dose delivered to the entire gland volume, comprised of the CTV, GTV and BTV. This focused IMRT treatment method, as described, is currently utilized in only a minority of select academic settings using functional images acquired with either Magnetic Resonance Spectroscopy Imaging (MRSI) or Single Photon Emission Computerized Tomography (SPECT) images to help define a region within the prostate gland believed to represent occult tumor volumes. These identified areas found to be suspicious for occult tumor on functional imaging represent findings which are indistinguishable with standard anatomic studies such as Computerized Axial Tomography (CAT or CT) scan, Magnetic Resonance Imaging (MRI) used in conjunction with Ultrasound (US) and/or US alone. While the SPECT imaging techniques rely on overexpression of a specific protein identified by a radiolabeled monoclonal antibody, the MRSI technique utilizes voxel analysis of tissue composition to detect regions felt more likely to represent cancerous regions. Newer functional studies will certainly be developed in the future using similar technologies, such as Positron Emission Tomography (PET) tracers, Optical Biopsy techniques, or other similar technologies.

Cancer patients, such as those with prostate cancer, are frequently followed for extended time periods between diagnosis, medical imaging, treatment and post-therapy follow-up. These patients are, therefore, evaluated over time by different physicians (e.g., urologists and radiation oncologists) in a number of settings (e.g., physician office, outpatient hospital imaging, surgical center) and with various imaging and image-guided treatment modalities requiring different patient positioning during imaging (supine) and treatment (lateral decubital) which, collectively, serve to obscure correlation of pathology information with in-vivo image sets.

Thus, there remains a need for the ability to refine the identification and volumetric location of disease as correlated to positive histopathology within the suspect organ or tissue, and to be able to use these refined data sets in a more informed manner that will lead to more efficient subsequent interventions, such as repeat biopsy, that may ultimately lead to the ability to direct therapy in a more effective and less harmful manner. It has been estimated that each year in the U.S. over one million biopsies are performed, with as many as 50% of those core samples being reported as negative. With standard core biopsy sampling techniques for the prostate gland collecting 6 to 12 standard core samples per patient, millions of core tissue biopsy samples are evaluated each year. The clinical inefficiency of the biopsy procedure results in a large negative burden to patients for non-productive procedures correlating to increased risk for procedure related morbidities (e.g., fever, infection, erectile dysfunction, bleeding, discomfort, and lost productivity), for the often ineffective procedure. In addition, the pathology results are routinely lost to discreet anatomic localization for use in therapy planning and therapeutic dose modulation.

BRIEF DESCRIPTION

The present disclosure thus relates to systems, methods, apparatuses, and devices by which biopsy tissue sample data may be retained and correlated with images to create a patient specific record of normal tissue, abnormal tissue, and tumor/disease-containing volumes within a patient following biopsy specimen analysis and recording. After a columnar biopsy specimen is taken from a target tissue of a patient, the location of the biopsy cavity is recorded by for example placement of a fiducial marker oriented in the same location and direction as the biopsy specimen. Alternatively, the biopsy instruments, e.g. biopsy needle tip, may be recorded by 3D coordinate positioning within a biopsy-guidance image software, or via electronic signals, for example ultrasound and/or MRI based using transrectal or transperineal transducers. The biopsy specimen is then placed in a biopsy tracking cassette that contains a plurality of coded zones (usually by color). The biopsy specimen is thus divided into regions with different codes. When tumor/disease is located, the particular region of the tumor/disease of the biopsy specimen can be identified, and that region can be correlated with a specific location within the target organ of the patient based on the orientation of the fiducial marker or the tracked virtual marker within biopsy guidance software. This permits further localization of normal and tumor/disease to a particular location in the target tissue of the patient, so that normal, abnormal and diseased regions can be tracked and correlated with images to enable more informed repeat medical interventions and treatment modulation that can be directed to a smaller volume with a reduced margin beyond the target aimed at improved clinical outcomes.

Particularly disclosed in various embodiments herein are methods of identifying a localized area of a target tissue. A biopsy device is used to access the target tissue, the biopsy device comprising: (i) a trocar having a cannula with a blunt first end and a cupped second end; and (ii) a stylet having a conical tip at a first end and a cap on a second end, wherein the stylet is inserted into the cannula so that the conical tip extends beyond the blunt first end of the trocar. The cap of the stylet is sized to engage the cupped second end of the trocar and prevent passage of the second end of the stylet into the cannula. The stylet is then removed from the trocar and a biopsy needle is inserted through the trocar. The biopsy needle is used to obtain a columnar biopsy specimen from the target tissue at a biopsy location. The biopsy specimen is a long, thin column, and can be considered to have a proximal end and a distal end. The columnar biopsy specimen is then deposited in a biopsy tracking cassette which comprises a surface with a plurality of coded zones in a single column. The columnar biopsy specimen is deposited so as to rest across the plurality of coded zones such that the columnar biopsy specimen is differentiated into a plurality of regions. Next, at least one fiducial marker is placed and oriented substantially at the biopsy location so that the at least one physical or virtual fiducial marker correlates with the proximal end and the distal end of the columnar biopsy specimen. The biopsy specimen is analyzed to identify a particular region of the biopsy specimen. Generally, the particular region will show signs of tumor or other disease. The location of the particular region of the biopsy specimen can then be correlated with the orientation of the fiducial marker at the biopsy location to identify the localized area of the target tissue of the patient that should be further examined and/or treated.

The methods may further comprise obtaining at least one image of the target tissue to detect a location of the at least one fiducial marker after placing and orienting of the at least one fiducial marker. At least one image obtained using cross sectional or anatomic scanning, such as computed tomography (CT), magnetic resonance imaging (MRI), ultrasound (US), X-ray, fluoroscopy, and in combination with a metabolic or functional scanning, such as SPECT, PET, multi-parametric MRI (for example diffusion weighted imaging (DWI), Dynamic Contrast Enhanced Imaging (DCE), or spectroscopy MRI or MRSI), optical biopsy, in combinations and/or hybrids thereof.

In particular embodiments, multiple columnar biopsy specimens are obtained from the target tissue at multiple biopsy locations and different fiducial markers are placed and oriented at each biopsy location, the different fiducial markers being distinguishable from each other on an image of the target tissue. The different fiducial markers can be distinguished based on their size, shape, image intensity, acoustic impedance, wavelength, or combinations thereof via a permanent or temporary physical fiducial marker placed in-situ at the approximate location of the biopsy tissue cavity, and/or tracking the location of a temporary fiducial marker as in the case of the needle tip of a trocar, biopsy needle or other tissue sampling apparatus used to extract or locate the biopsy cavity with software tracking in an image guidance system such as in the example of transrectal or transperineal ultrasound (TRUS or TPUS) and/or MRI guided biopsy procedures.

The methods of the present disclosure may further comprise treating the localized area of the target tissue within the patient with an applied therapy. In specific embodiments, the applied therapy is selected from IMRT, EBRT, cryotherapy, LDR, HDR, hyperthermia, photodynamic therapy, HIFU, and gene therapy.

The coded zones in the biopsy tracking cassette may each include a different colored dye to identify different regions on the columnar biopsy specimen. However, other means are contemplated for identifying the different regions (e.g. materials that look different in an image) or via temporary or virtual fiducial markers.

The fiducial marker can be correlated with both the columnar biopsy specimen and the biopsy tracking cassette.

Also disclosed in various embodiments herein are biopsy tracking kits, comprising: a trocar, a stylet, a biopsy needle, a biopsy tracking cassette, and at least one fiducial marker. The trocar has a cannula with a blunt first end and a second end with a cup. The stylet has a conical tip at a first end and a cap on a second end, the cap being sized to engage the cup of the trocar and prevent passage of the second end of the stylet into the cannula. The biopsy needle is used to obtain biopsy specimens, and when inserted through the trocar, extends beyond the blunt first end for a distance of generally from about 15 mm to about 25 mm. The biopsy tracking cassette comprises an internal surface with a plurality of coded zones in a single column. The at least one fiducial marker can be distinguished on a radiological image.

The cup of the trocar can be in the shape of a cone, and is generally adapted to receive the conical tip of the stylet. The conical tip of the stylet can extend at least 0.5 cm beyond the blunt first end of the trocar when fully inserted through the trocar. The cap of the stylet can be in the shape of a right conical frustum.

In specific embodiments, the internal surface of the biopsy tracking cassette is a mesh, and the plurality of coded zones is arranged in a single column from a distal end of the internal surface to a proximal end of the internal surface.

The biopsy tracking cassette may comprise a lid and a housing for the internal surface. Sometimes, the housing and the lid of the biopsy tracking cassette are formed as a single piece. The housing and the lid of the biopsy tracking cassette can include pores for fluid exchange/drainage.

In particular embodiments, the fiducial marker has a length that is about equal to the length of the columnar biopsy specimen, i.e. from about 15 mm to about 25 mm. In more specific embodiments, the fiducial marker has spaced apart markings that are visually distinguishable on a radiological image.

Also disclosed in embodiments herein are biopsy tracking cassettes comprising one or more compartments, each compartment containing an internal surface with a plurality of coded zones arranged in a single column from a distal end of the internal surface to a proximal end of the internal surface.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 3A is one embodiment of a fiducial marker containing markings for identifying more specific or particular regions/areas in a target tissue.

FIG. 3B is another embodiment of a fiducial marker containing markings for identifying more specific or particular regions/areas in a target tissue.

DETAILED DESCRIPTION

Figure 1:
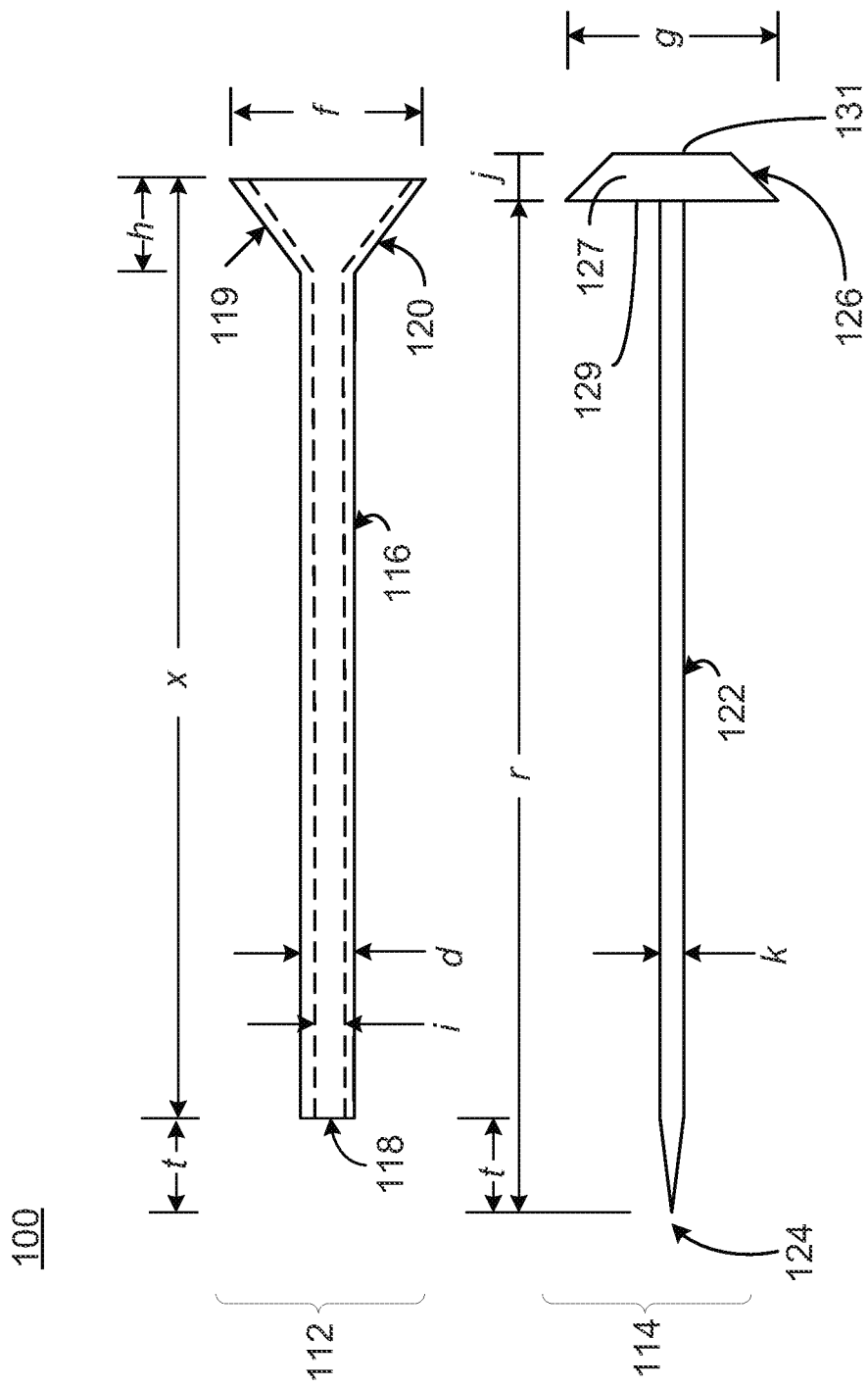
FIG. 1 illustrates a trocar and a stylet of the biopsy kit of the present disclosure.

A more complete understanding of the devices, components, and methods disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

Numerical values should be understood to include numerical values which are the same when reduced to the same number of significant figures and numerical values which differ from the stated value by less than the experimental error of the conventional measurement technique used to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. The term "substantially" can refer to plus or minus 5% of the indicated number.

As used in the specification, various devices and parts may be described as "comprising" other components. The terms "comprise(s)," "include(s)," "having," "has," "can," "contain(s)," and variants thereof, as used herein, are intended to be open-ended transitional phrases, terms, or words that require the presence of the named component and permit the presence of other components. However, such description should be construed as also describing the devices and parts as "consisting of" and "consisting essentially of" the enumerated components, which allows the presence of only the named component, and excludes other components.

The term "anatomic image" is used throughout the specification to refer to imaging techniques that use cross sectional scanning to create visual anatomic representations of the body for analysis or treatment. Those techniques may include computed tomography (CT), magnetic resonance imaging (MRI), ultrasound (US), X-ray, fluoroscopy. The term "functional image" is used throughout the specification to refer to imaging techniques that may use single-photon emission computed tomography (SPECT), positron emission tomography (PET), magnetic resonance imaging with multiparametric sequences (mp-MRI) such as DCE, DWI, MRIS, and optical fluorescence, among others. These images may be fused and or co-registered with a single or multiple data sets. The term "image" should be considered as including functional images, anatomic images, real-time images, and saved/stored images using radiation or any other means of anatomic and functional scanning utilized to represent in-vivo representations of the body.

As noted, a key issue for local cancer therapies such as radiation oncology is the term "dose response", stating that cancers such as prostate cancer have a higher cure rate for a higher delivered dose. With Intensity Modulated Radiation Therapy (IMRT) or other local therapies such as cryotherapy, focal cryotherapy, thermotherapy, chemoembolization and photodynamic therapy, physicians can "paint" a high dose of the local therapy to relatively small volumes. However, what is lacking is an ability to accurately identify discrete areas of tumor, such that unintended treatment to surrounding tissues can be minimized. This can be useful for cancers in organs such as the prostate, kidney, liver, pancreas, and the breast.

Previous methods of identifying local volumes for treatment have been described in U.S. Pat. No. 7,831,293, which is fully incorporated herein by reference. Very generally, those methods placed an image-detectable marker at the site of each biopsy at the time of the biopsy procedure. The marker could then be visualized and tracked after the procedure to provide specific correlation to point locations of either benign or cancerous tissue. The markers could also be used during repeat biopsy, or to help direct therapy for the patient. The therapeutic dose to the tumor could be increased while simultaneously sparing excessive therapy to regions believed to be unlikely to contain disease. The information and data subsequently gathered from the correlation of specific markers with specific biopsy specimens was also most helpful when imaging, diagnoses and treatment are obtained or performed by different physicians, at different facilities and at different times, which may occur.

In the present disclosure, a biopsy is conducted to obtain a columnar biopsy specimen from a target tissue of the patient at a given biopsy location. The columnar biopsy specimen is generally in the form of a thin column, and has a length from about 15 millimeters (mm) to about 25 mm, or more specifically from about 18 mm to about 22 mm. The biopsy specimen has a proximal end and a distal end, relative to the location from which the biopsy is being taken. After the biopsy specimen is removed from the patient, one or more fiducial markers are inserted at the biopsy location and oriented to identify the locations where the distal end of the biopsy specimen and the proximal end of the biopsy specimen were located. The columnar biopsy specimen itself is differentiated into a plurality of regions, using for example a different colored dye in each region. After examination/analysis, if a tumor/disease is found in a particular region of the biopsy specimen, the location of that particular region in the target tissue can be identified based on the location of the fiducial marker(s) at the biopsy location, and can be localized to a smaller volume than the fiducial marker(s).

Also disclosed herein are biopsy kits for performing the methods described above. Generally, the biopsy kits include a trocar, a stylet, a biopsy needle, a biopsy tracking cassette, and at least one fiducial marker. Other components of such kits can include other items useful for such procedures, such as: a sterile drape, mesh (e.g. nylon, gauze, PTFE), formalin (for fixing the biopsy specimens), ink and swabs for marking, labels for the cassettes, and an insertion needle for the fiducial marker.

These medical kits enable tracking of the biopsy tissue for retention of in situ spatial orientation, tissue type, and composition. The kits contain systems that enable directed biopsy at a given site with image sets shown to be suspicious for tumor burden, and enable biopsy sample collection and positioning of a fiducial marker within the biopsy cavity. The collected tissue can be displayed with markings that uniquely label the tissue and any fragments for correlation of the precise location from which the biopsy sample was derived. The fiducial marker can be temporary or permanent, and should be visible on an anatomic or functional image, and may be represented as a virtual marker whose location is acquired or tracked using an instrument such as a needle or needle tip at the time of biopsy.

A primary benefit of such a surgical kit will be to promote and retain biopsy core tissue samples for concordance with pathology, subsequent correlation with pathology data (e.g. percent core positive sample, location of the sample within the organ, and within a single core), permitting the X-Y-Z orientation of the biopsy core sample with anatomic or functional image references. Positive disease will be incorporated into treatment planning software for image guided interventions with treatment remodulation to intensify doses to positive disease areas (e.g. Gleason 7) while reducing doses in areas shown to be negative for tumor or areas containing normal critical structures (e.g. neurovascular bundle, rectum, urethra). Such a kit will also encourage adoption of image guided biopsy procedures, encourage biopsy sample marking, and avoid repeat biopsies and blind biopsies. Such a system will enhance data collection from biopsy procedures, making them available in the medical record to guide subsequent interventions.

Included in the biopsy kit 100, and used in the methods described herein, are a trocar and stylet as illustrated in FIG. 1. The trocar 112 is shown on top, and the stylet 114 is shown on the bottom. The trocar 112 includes a cannula 116 that has a blunt first end 118 and a second end 120 spaced apart at the other end of the cannula. The cannula is a hollow tube through which various implements, such as the stylet and the biopsy needle, can pass. The cannula has an outer diameter d and an inner diameter i. The first end 118 of the trocar is blunt, and is not configured for cutting. Put another way, the surface of the first end is perpendicular to the surface of the cannula.

The second end of the trocar includes a cup 119 that is shaped to permit the user to safely grip and manipulate the trocar, e.g. between two fingers. The cup may be described as having a conical shape or a funnel shape, with the vertex of the cone/funnel connecting to the cannula 116. Implements are inserted at the base of the cup, which is marked as having a diameter f and a length h. The wall of the cup can also be described as tapering smoothly from diameter f to diameter d. The shape of the cup encourages insertion of various needles into the trocar 112 while protecting the user's fingers and reducing needle sticks to the healthcare practitioner. The cup 119 can be manufactured as part of the cannula 116, such as a flared end, or affixed as a separate component, e.g. welded. A dotted line shows the inner surface of the trocar.

The stylet 114 includes a rod 122 configured to be inserted and slide within the cannula 116 of the trocar. The rod 122 terminates at a first end with a conical tip 124, and at a second end 126 with a cap 127. The rod is contemplated as being solid, and has a diameter k. The conical tip 124 is not beveled, and provides a cutting edge. The cap 127 is sized to engage the cup 119 of the trocar and prevent the second end of the stylet from passing into the cannula of the trocar, i.e. to prevent the user from losing control of the stylet. The base of the cap 127 has a diameter g and a length j. The diameter g of the base of the cap is always greater than the outer diameter d of the trocar.

The cap 127 can generally have any shape that prevents passage of the stylet 114 into the cannula 116 and permits the user to manipulate the stylet. For example, it may be permissible for the cap 127 to have a diameter g that is between outer diameter d and cup base diameter f, as long as the cap has a height j that is sufficiently larger than cup height h. In this situation, the cap 127 is seated within the cup 119. Alternatively, as illustrated here, the cap 127 is in the shape of a right conical frustum having a base 129 and a top 131. The base is oriented towards the rod 122, and the top is oriented away from the rod. The diameter g is greater than the diameter f, so that the cap 127 of the stylet does not enter the cup 119 of the trocar at all. In particular embodiments, the cup 119 of the trocar has a diameter f of at least 0.3 centimeters (cm), and may be from 0.3 cm to about 3 cm. The base diameter g of the cap of the stylet is, in particular embodiments, greater than the diameter f of the cup 119 of the trocar.

The length x of the trocar runs from the first end 118 to the second end at the base of the cup 119. As previously mentioned, the cup has a length h. In addition, a distance t beyond the first end 118 is shown. The rod 122 of the stylet 114 has a length r from the conical tip 124 to the base of the cap 127. As previously mentioned, the cap has a length j. In particular embodiments, the stylet length r is the sum of (x+t) when the cap 127 has a diameter g greater than the diameter f. More specifically, the stylet length r is greater than trocar length x, such that the distance t is from about 3 mm to about 10 mm (0.3 cm to 1.0 cm), so that the conical tip 124 of the stylet extends beyond the blunt first end 118 of the trocar when fully inserted through the trocar.

The length x of the trocar can vary as desired to permit access to relevant organs or tissues. In particular embodiments, the length x can vary from 6 centimeters up to 25 centimeters, or in more specific embodiments from 16 cm to 20 cm. Similarly, the inner diameter i and outer diameter d of the cannula can vary as needed. In particular embodiments, the cannula is a needle having dimensions of 12 gauge to 20 gauge (Stubs/Birmingham system, not French).

In particularly contemplated embodiments, the trocar has a length x of 16 cm and is a 17 gauge needle with an outer diameter of 1.473±0.013 mm, and an inner diameter of 1.067±0.038 mm. In particularly contemplated embodiments, the stylet has a diameter k that fits within the 17 gauge needle, i.e. is less than 1.067 mm.

The trocar 112 and stylet 114 are manufactured from materials applicable to sterile applications, such as surgical steel. These parts can be for a single use, e.g. disposable, or repeated use, e.g. capable of being sterilized. It is noted that the blunt first end 118 of the trocar and the conical tip 124 of the stylet are radially symmetrical. This minimizes the movement of tissue in the target tissue of the patient during insertion, compared to a beveled edge which pushes the tissue in one direction away from the cannula and will change the positioning of the tissue that is biopsied.

If desired, a disposable reverse tweezer or hemostat may be included e-like clamping attachment to the trocar for holding the trocar steady whilst the re-usable biopsy needle is reinserted to the trocar thus improving user safety by extending the user's hands further away from the needle at the time of reintry to the cupped end of the trocar to lessen the opportunity for a dirty needle stick during re-use of the biopsy needle.

The biopsy needle, if included in the surgical kit, can be any standard biopsy needle known in the art, and should also fit through the cannula of the trocar. Biopsy needles are commercially available from suppliers such as Bard, Cook Medical, CareFusion, and Medax that are typically about 25 cm in length. Referring back to FIG. 1, the biopsy needle is selected to extend a distance t of about 15 mm to about 25 mm beyond the first end of the trocar, or in more specific embodiments a distance t of about 18 mm to about 22 mm. The biopsy needle is used to obtain a columnar biopsy specimen from the target tissue of the patient at a desired biopsy location. The resulting biopsy specimen will have a distal end and a proximal end, and a length t corresponding to the distance through which the biopsy needle extends beyond the trocar. It is noted that the biopsy needle may be implemented in the form of a biopsy gun.

The trocar design improves patient safety by enabling a reduction in the total number of needle sticks required to achieve a typical "sextant" biopsy approach. By inserting and advancing the trocar to the farthest end of the gland to acquire tissue and then moving the trocar sequentially and proximally out of the gland, additional biopsy needles may be inserted through the trocar as the trocar is withdrawn thereby allowing multiple biopsy samples to be acquired through a single needle stick through the patient and organ, instead of requiring multiple needle sticks. This can reduce the incidence of cross contamination (for example in a transrectal approach with fecal material) that is associated with infection, bleeding, trauma and damage to normal pelvic structures such may be associated with procedure related erectile dysfunction.

Figure 2A:
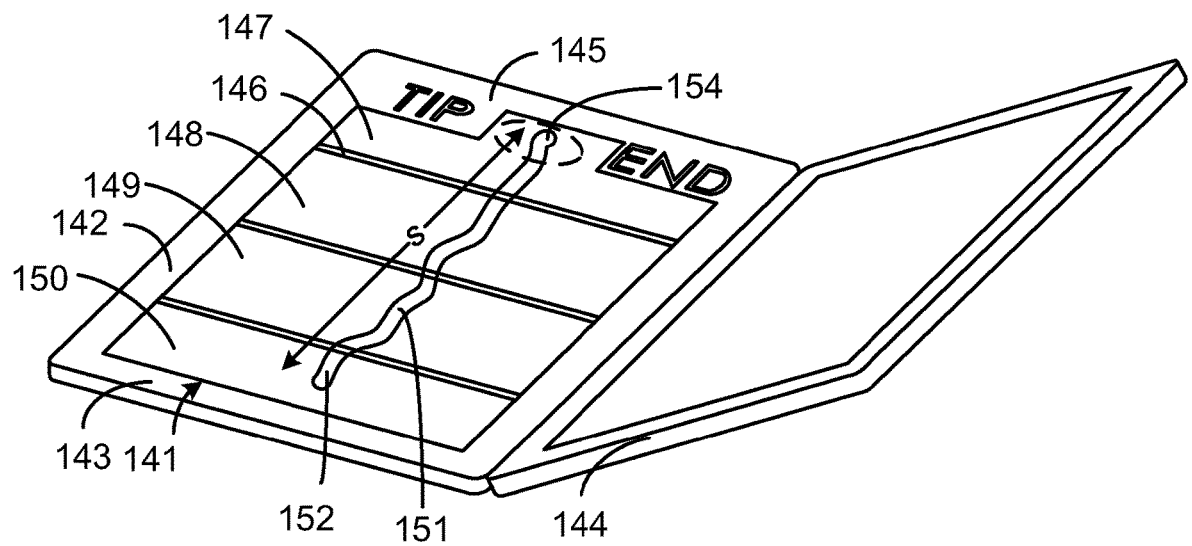
FIG. 2A is a view of one embodiment of a biopsy tracking cassette with the lid open.
Figure 2B:
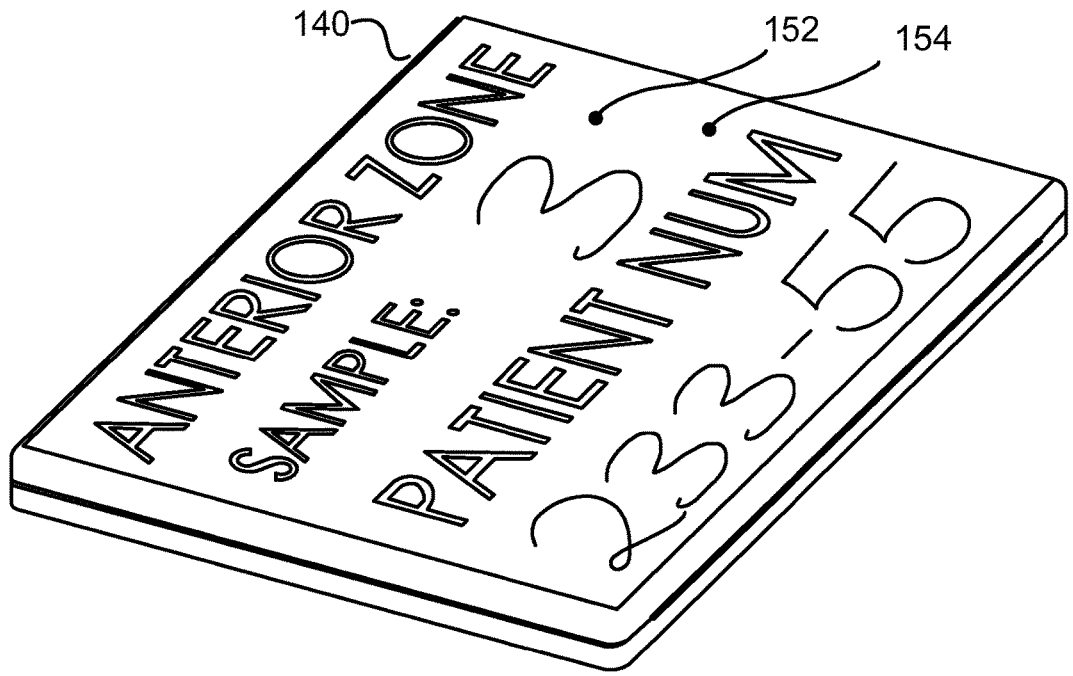
FIG. 2B is a view of the embodiment of the biopsy tracking cassette of FIG. 2A with the lid closed.

Also included in the surgical kit is a single-compartment biopsy tracking cassette in which a single columnar biopsy specimen is placed. This biopsy tracking cassette 140 is illustrated in FIG. 2A in an open configuration with a deposited columnar biopsy sample. The exterior of the tracking cassette 140 is illustrated in FIG. 2B in a closed configuration. The biopsy tracking cassette is molded from a high density polymer that is non-reactive with histological solvents, such as an acetal polymer. The cassette includes a housing 142 that forms a compartment 141. A lid 144 is also provided to close the compartment. The housing and the lid can be formed as a single piece, or may be formed as two separate pieces that are subsequently joined together. The lid can be opened and closed multiple times and lock securely each time. The single compartment may have dimensions of 25 mm length by 30 mm width. The compartment is generally deep enough to receive two layers of mesh. The housing may also include pores (not illustrated) for maximal fluid exchange/drainage. The pores can vary in size from 0.26 mm to 1.0 mm, and at 0.26 mm size the cassette may have over 2000 individual pores.

The compartment of the biopsy tracking cassette is sized to include an internal surface 146 upon which the columnar biopsy specimen is deposited/received. This internal surface is usually a mesh surface made of nylon, gauze, polytetrafluoroethylene (PTFE), and the like. The internal surface, as well as the cassette, each have a proximal end 143 and a distal end 145. A plurality of coded zones is arranged in a single column on the internal surface from the distal end to the proximal end. As illustrated here, there are four different zones 147, 148, 149, 150 running across the width of the internal surface, though of course any number of coded zones can be used. A columnar biopsy specimen 151 is shown here deposited across all four zones. As illustrated here, the internal surface 146 identifies the end at which the tip of the biopsy needle should be placed, so that the distal end of the biopsy specimen is consistently placed at the same location across multiple cassettes. This maintains the orientation of the biopsy specimen within the cassette relative to the biopsy location for subsequent record keeping.

The columnar biopsy specimen 151 has a proximal end 152 and a distal end 154, and a length s. As discussed above, the length s will be from about 15 mm to about 25 mm, or in more specific embodiments about 18 mm to about 22 mm. The coded zones are used to differentiate regions of the columnar biopsy specimen deposited across the zones. For example, each zone may have a different colored dye, which will adhere to the region of the biopsy specimen falling within that zone. The various colors should be selected to minimize conflict with any downstream pathological staining that may be used and to maximize contrast between the different zones; thus the selected colors may vary depending on the target tissue. The internal surface can be prestained with these dyes, or other similar markers, or the colors can be added after the biopsy specimen is deposited. The colored dyes localize regions of the specimen so that even if the specimen 151 is fragmented during transport, information about the location of each fragment is maintained for correlation back to the target tissue/organ. For example, with a 20-mm-long columnar specimen and four zones, the histopathology is localized to 5 mm segments of the columnar specimen. A second piece of mesh (not shown can be placed on top of the internal surface 146 and the biopsy specimen 151, between the lid 144 and the specimen.

FIG. 2B shows the exterior of the tracking cassette 140. The outer surface 152 includes a labeling surface 154 which can receive a unique label affixed with adhesive, or be written on directly. The unique label includes a bar code, in-vivo location, sample number, patient number, and/or the like to relate the biopsy specimen with a particular biopsy location, patient, etc.

Figure 2C:
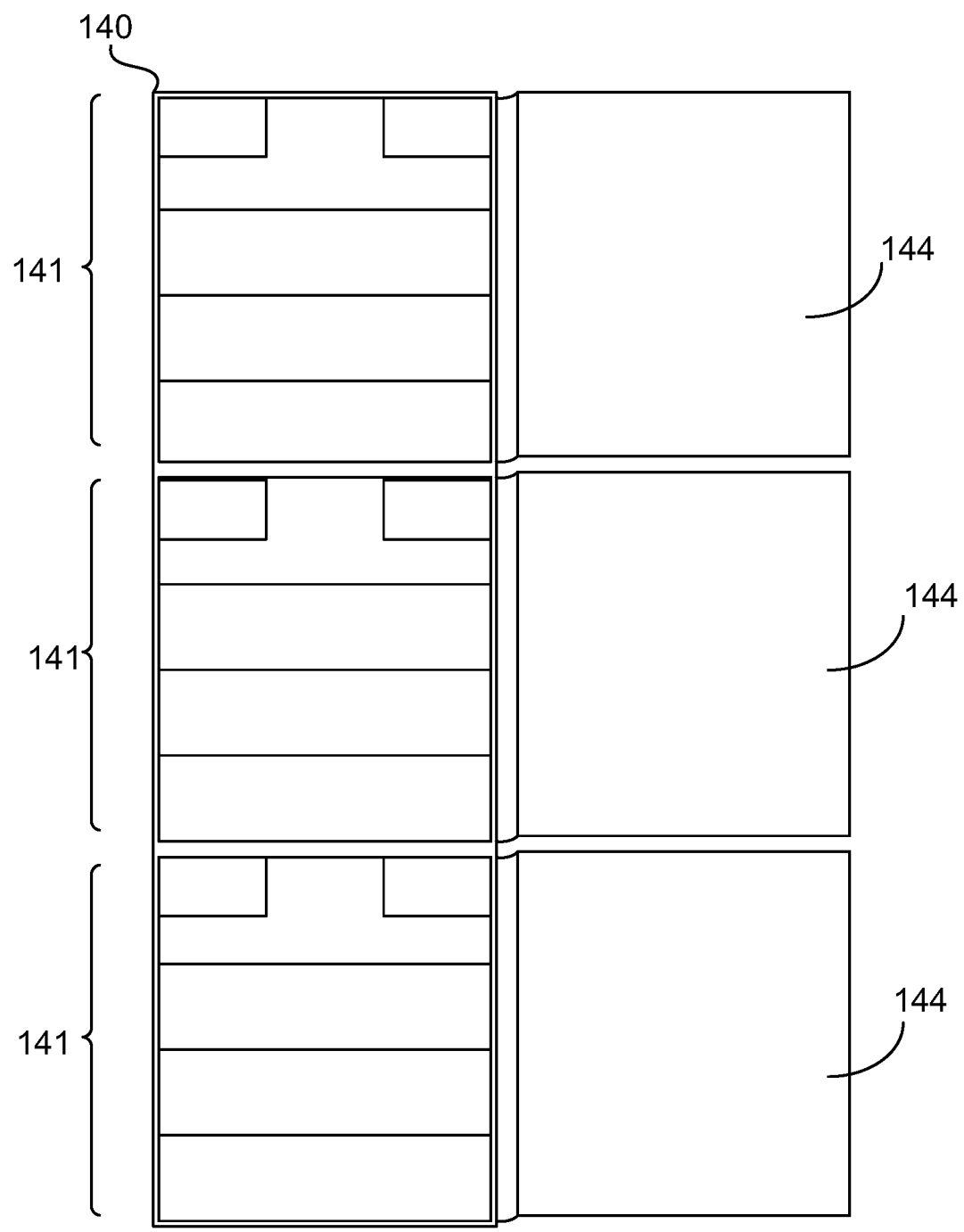
FIG. 2C is another embodiment of a biopsy tracking cassette, having multiple compartments, each compartment having a plurality of coded zones arranged in a single column.

FIG. 2C illustrates a multi-compartment embodiment of the biopsy tracking cassette 140. The biopsy tracking cassette 140 includes a housing that forms multiple compartments 141. Each compartment includes an internal surface with a plurality of coded zones arranged in a single column, and has its own lid 144. Each lid connects to the housing 142 and is capable of independent movement, e.g. separate opening and closing. The illustrated cassette has three compartments arranged in a 1×3 configuration. Generally, it is contemplated that the multi-compartment cassette can have configurations of n×m compartments where n and m are independently selected integers usually in the range of 1 to 10, such as 3×4, 3×5, 3×6, 4×3, 4×4, 4×5, 4×6, and the like. The multi-compartment cassette may have a total of 12 to 100 compartments, including a total of 12 to 36 compartments.

When used, the biopsy specimen should be deposited to retain its original length as much as possible. When the specimen is placed between a top mesh and a bottom mesh, and the compartment is then closed and exposed to fixative, the code in each zone (e.g. color) will adhere to the biopsy specimen in the given zone.

The biopsy kit also includes at least one fiducial marker that is detectable on an image. The detectable markers can be any suitable material that will function to produce an image, representative graph or signal for co-registration to the particular image modalities used so that the biological target areas or volumes which correlate to findings on the biopsy pathology report can be correlated with the location of the biopsy location and used to define a BTV or region of non-diseased tissue. Such markers can be in the form of physical clips, seeds, implants and the like, all as would be apparent to those of ordinary skill in the art in view of this disclosure. Alternatively, the fiducial marker may be represented by a virtual marker using an instrument such as a biopsy needle tip that is in contact with the tissue during the tissue extraction procedure and recorded in the biopsy guidance software.

As noted, suitable materials for said markers will depend upon the particular imaging modalities to be employed and the degree to which the markers must be distinguishable from one another by such modalities. Thus, desirable marker characteristics or combinations can be, depending upon the image modalities, image intensity, such as the degree of radiopacity, fluorescence or echogenicity, image wavelength, size, shape and so on. Suitable marker materials will include gold, titanium, tantalum, rhodium, platinum, silver, iodine, collagen-plug, stainless steel, coated lead, combinations thereof and the like.

In some embodiments, it may be desirable for the markers to be biodegradable. Such markers can be made from biodegradable and bioresorbable polymers, such as polymers and copolymers of alpha-hydroxy acids. Suitable polymers, such as polymers and copolymers of lactic acid, glycolic acid, lactide and glycolide can be prepared from or imbibed with materials having suitable radiopacity or other detectable qualities which, after providing their desired image, will degrade and be eliminated from the tissue over time. Thus, one can, for example, use a marker with a polylactic acid or other bioabsorbable material filled with iodine or other radiopaque material so that they are visible under X-ray or ultrasound. The radiopaque material may itself be bioabsorbable. Other suitable marker materials will be apparent to those of ordinary skill in the art in view of the instant disclosure.

In preferred embodiments, to facilitate tracking and recording, it is advantageous if the markers are visually distinguishable on anatomic or functional images. This is particularly desirable when subsequent biopsies are taken in the same general region of the target tissue. In this way, one can readily distinguish between, for example, right apex biopsy 1 and right apex biopsy 2. Thus, it will be apparent to those of ordinary skill in the art that the markers can be designed to provide visually distinguishable images each from the other, such as by shape, image intensity, wavelength or the like. For example, Visicoil® markers, commercially available from IBA, Louvain la-Neuve, Belgium, are available in various lengths, which can be recorded into the data set for future reference. Similarly, Gentra Source, from Kawasumi Laboratories America, Inc., provides a fine-wire coiled Rhodium structure which provides a unique image on CT. Still further, Best Gold 198 Seed inactive and fiduciary marker kits from Best Medical International, Inc., provide gold markers of varying dimensions (0.8 mm diameter in 3, 5 and 7 mm lengths; 1.0 mm diameter in 3, 5, 7 and 10 mm lengths; and, 1.2 mm diameter in 3 mm lengths), which can provide unique MRI and CT signals depending upon the marker diameter and length.

Similarly, non-radioactive so-called "cold seeds" may be commercially available which will produce unique image patterns. Various seed companies, such as Theragenics and Best produce seeds which have unique design characteristics which are visually distinguishable on Xray or Fluoroscopy. Likewise, while most seeds are not visually distinguishable on CT or MRI, seeds with a high volume gold content may be detectable on MRI. Other suitable markers which may be visually distinguishable on various imaging modalities include a non-radioactive or "cold" TheraSeed Pd-103 from Theragenics, which will provide unique identification on X-ray or Fluoroscopy and a cold Iodine-125 Cold Echo Seed, from Amersham-GE Medical, which will provide unique identification on X-ray, Fluoroscopy and ultrasound. Biopsy site markers may be selected to include other functions, such as implanted electromagnetic transponders (Calypso® 4D Localization System, Calypso Medical) that track patient motion during fractionated dose treatments and metal oxide semiconductor field-effect transistor technologies (OneDose Patient Dosimetry System, Sicel Technologies) designed for in vivo measurement of patient dose during radiotherapy.

Alternatively, a "virtual" fiducial marker can be defined using software packages designed for image guided biopsy procedures using, for example transrectal ultrasound probes that may be fused with other image sets such as MRI with multiparameteric sequences and software tracking as available from Artimus (Eigen), Uronav (Philips) and Symphony (MIM software). These data sets may then be combined with subsequent therapeutic treatment planning software for guided interventions.

In particular embodiments, the fiducial marker has a length that is about equal to the length of the columnar biopsy specimen, i.e. from about 15 mm to about 25 mm, or in more specific embodiments from about 18 mm to about 22 mm. It is also contemplated that in particular embodiments, the fiducial marker includes markings which are spaced apart and are visually distinguishable on a functional or anatomic image. These markings can visually separate the biopsy location into different regions corresponding to the different regions on the columnar biopsy specimen.

Two contemplated and non-limiting examples of such a fiducial marker are shown in FIG. 3A and FIG. 3B. FIG. 3A is a side cross-sectional view of a fiducial marker 200. This contemplated example is made from two different sets of rings 210, 220. Each set of rings has a central hole 212, 222, which are of the same diameter. The rings 210 are detectable by radiological imaging, whereas the rings 220 are radiotransparent, i.e. cannot be detected by radiological imaging. As illustrated here, the rings 210 also have a different shape from the rings 220; the radiotransparent rings 220 are more cylindrical. The rings are held in place relative to each other by a core 202 that passes through the central holes 212, 222 and caps 204 at each end of the core. The core and caps are also radiotransparent. As illustrated here, there are five rings 210 and four rings 220. These rings can be used to identify four areas in the target tissue that correspond to the four coded zones of the biopsy specimen illustrated in FIG. 2A. The rings 210 generally have the same length, and the rings 220 have the same length (running between the ends 204). As an alternative, the rings 210 could be separated by fixed distances, e.g. every 2 mm along the marker.

FIG. 3B is an external view of a second exemplary fiducial marker 200. Again, there are five markings 230 spaced apart by four regions 240. The marker is made from a radiotransparent material, such that the four regions 240 are radiotransparent. The five markings can be made by applying a thin film of a detectable material upon the marker. Again, the markings can be used to identify four areas in the target tissue that correspond to the four coded zones of the biopsy specimen illustrated in FIG. 2A. The markings 230 generally have the same length, and the regions 240 have the same length (running between the ends of the marker).

As previously mentioned, it is contemplated that multiple biopsy specimens can be obtained from different biopsy locations. When this is done, each biopsy specimen should be placed in its own tracking cassette, and each biopsy location should receive a separate fiducial marker that is distinguishable from the other markers. This permits a particular fiducial marker to be correlated with a particular columnar biopsy specimen and a particular biopsy tracking cassette. For example, a fiducial marker may have a unique RFID tag number which can be recorded with the biopsy specimen.

Figure 4C:
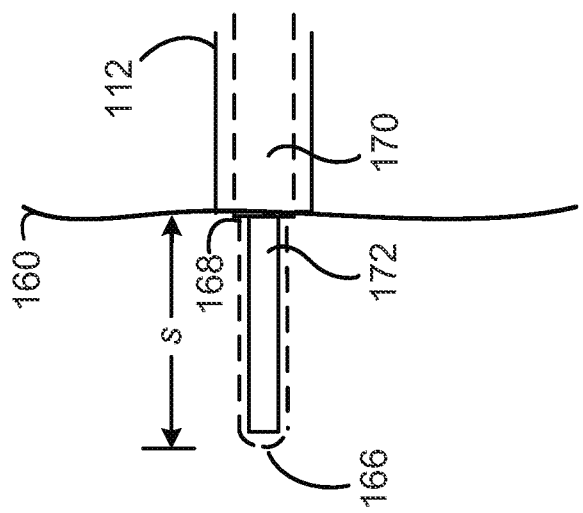
FIGS. 4A, 4B, and 4C schematically illustrate a process of obtaining a biopsy specimen from a target tissue of a patient.
Figure 4B:
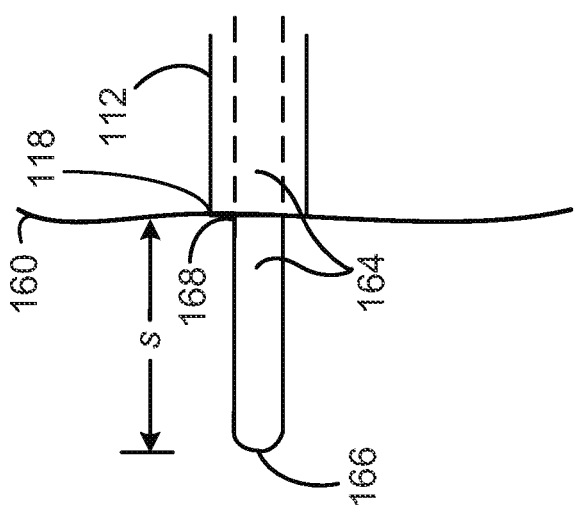
Figure 4A:
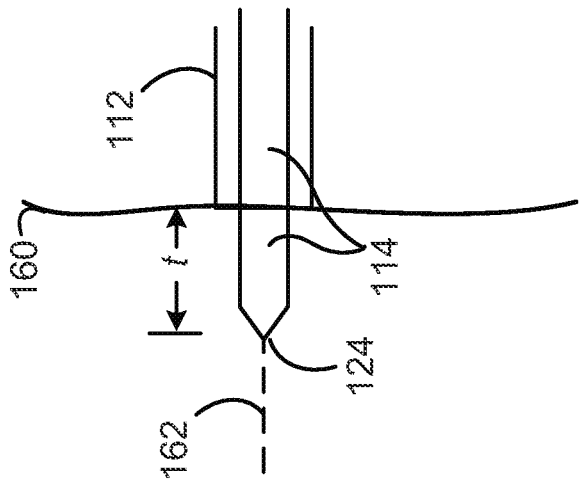

FIGS. 4A-4C illustrate several of the methods and components of the present disclosure. These figures schematically illustrate the use of the surgical kit for obtaining a biopsy specimen from a target tissue 160 at a biopsy location. The target tissue can be prostate tissue, breast tissue, liver tissue, renal tissue, and the like.

Beginning with FIG. 4A, the stylet 114 is fully inserted in the trocar 112, so that the conical tip 124 of the stylet extends beyond the blunt front end 118 of the trocar. The conical tip penetrates the target tissue 160 along a needle path 162 (indicated by dotted line) for a distance t.

In FIG. 4B, the trocar 112 remains in position, and the stylet 114 is removed. A biopsy needle 164 is subsequently inserted through the trocar 112. The biopsy needle 164 extends beyond the first end 118 for a distance s, which can be for example 18 mm to 22 mm. The biopsy needle 164 excises a columnar biopsy specimen (not visible) of length s. The biopsy specimen and the biopsy location will have a distal end 166 and a proximal end 168. The distal end of the biopsy specimen is oriented to a distal end of the biopsy needle 164. The biopsy needle is then withdrawn or removed from the trocar 112, and the biopsy specimen is deposited in a biopsy tracking cassette as previously described, such that the coded zones in the tracking cassette differentiate the columnar biopsy specimen into a plurality of regions.

Next, an image detectable marker is placed directly at the site where tissue was extracted for histological evaluation. Preferably markers are placed at multiple biopsy locations and, more preferably, at each biopsy location. Still more preferably, the markers are uniquely identifiable on imaging. Desirably, the marker will be placed at the biopsy location substantially simultaneously with the excision of the tissue from the biopsy location.

As illustrated in FIG. 4C, a fiducial needle 170 is inserted in the trocar 112. The fiducial needle is tipped with a fiducial marker 172, that is detectable in an anatomic or functional image. The fiducial needle 170 is used to place the fiducial marker 172 into the target tissue in the space previously occupied by the biopsy sample tissue removed by the biopsy needle. The fiducial marker 172 can be permanent, or temporary. The fiducial marker 172 is placed and oriented to correlate with the biopsy sample. In other words, the fiducial marker indicates where the distal end 166 and the proximal end 168 of the biopsy specimen were located.

The tissue specimens obtained at biopsy can then undergo pathology lab analysis to identify histopathologic evidence of tumor. A finding of positive (+) biopsy represents the definitive diagnosis of presence of disease. Thus, one can generate a data set comprising a series of marker locations, e.g., right apex, left apex and base, with their respective pathologies, e.g., benign, cancerous, benign. Preferably, the pathology reports will not merely provide evidence of the presence or absence of disease, they will evaluate the tumors for aggressiveness of disease and include other pathological data which can be included in the data set to be correlated to the fiducial marker sites. Additional pathology data which can be included in the data set correlated to each fiducial marker site can include genetics, genetic markers, genomics, proteomics, percent tumor burden, Gleason score, tumor marker positive, PSA, percent fee PSA (PSA II), other cancer antigens, prostatic acid phosphatase (PAP), free testosterone, total testosterone, optical biopsy, prostatic intraepithelial neoplasia (PIN) status, metastatic phenotypes, gene expression signature, and the like.

Again, it is important to be able to correlate the biopsy specimens with their corresponding fiducial marker so that the subsequent pathological analysis of the biopsy specimen and identification of disease in a particular region of the biopsy specimen can be correlated to a localized area in the target tissue. This enables one to visually identify the localized area of the target tissue based on the location and orientation of the fiducial marker on an image thereof. The fiducial marker images can be correlated with their respective biopsy specimens by any suitable means as would be apparent to those of ordinary skill in the art in view of the instant disclosure.

In its simplest form, each biopsy specimen can be correlated to a fiducial marker location by manually recording the marker type and marker location at the time of excision. More sophisticated techniques involving coordinate grids, computer software and tracking modalities may also be employed. For example, the patient's first biopsy procedure is frequently completed with the patient in lateral decubitus position in the urologist's office utilizing a Trans-Rectal Ultrasound (TRUS) probe for imaging. The biopsy specimens are extracted from each biopsy needle and placed into individual sample transport cassettes, tubes or similar appropriate packaging to protect and preserve the tissue sample. The outer packaging of the tissue transport system (cassette, tube, etc.) may be marked with directions and/or pathology prescription for sample processing. For example, the pathology prescription may request that the sample be recorded as to glandular location such that the histopathology report will track and report tissue sample findings with respect to biopsy tissue locations (e.g., base/apex, right/left side, lateral/medial). The biopsy specimens may further be described with respect to unique identifiers associated with the target tissue and fiducial marker location. This may be accomplished by tracking unique markers with, for example, numeric, alphabetic or alpha-numeric systems which are recorded manually or otherwise in the patient file, image set, CD, DVD or video recording and on each sample transport package for histopathology sample tracking.

Alternatively, software systems may be employed, such that the fiducial marker record with pathology specimen identifiers are loaded into a computerized tracking or software device either during the procedure or translated to the computerized patient record from notes made at the patient table post-procedure. Still further, the surgical kit may be provided with unique marker identifiers, such as pre-printed bar code stickers, so that each biopsy specimen can be correlated to a specific fiducial marker, in addition to the biopsy site gross anatomic determinants (e.g., apex base, right/left, medial/lateral). Such software will preferably be able to load detailed location information into the computer and be input or printed at the time the individual biopsy specimens are labeled.

In still further embodiments, more elaborate biopsy planning and correlation procedures can include a stepper carriage with an attached acrylic rectangular template mounted to a stand or operating room table for stabilization during the image assisted procedure. A biplanar ultrasound probe, MR or MR rectal array probe, or CT guided system may be connected to the template/stepper carriage. A series of, for example, transverse ultrasound views 5 mm apart from the base to the apex of the prostate may be obtained. The location of the urethra and rectum at each of these levels may be recorded and stored. Prior to biopsy needle placement, the probe may be placed at the reference plane and the contours of the prostate gland and anterior rectal wall outlined. The course of the urethra can be shown in overlay. The needle location may be tracked utilizing a biopsy needle with echogenic tip visible on the ultrasound. The actual location of each needle in the reference plane may be measured and fiducial marker positions recorded with reference to location relative to urethra, base and apex of prostate and anterior rectal wall. These images define the depths of the "base plane," "apex plane," and "reference plane." The location of the base plane determines the depth of biopsy needle insertion. As each needle is placed, its template coordinates (i.e., column and row) may be entered into the planning system and its actual location in the reference plane digitized with a pointing device, this being representative of "virtual" marking of the biopsy location using the biopsy instrument as the temporary fiducial marker. Together with the previously determined location of the template, planning systems may calculate the needle trajectories.

Images may be displayed on the live ultrasound image, for example, at each contour level, and this record may be saved on the computerized treatment planning programs. Spot fluoroscope images may be acquired to record marker placement for post-implant record correlation. Newer computer-aided 3-D treatment planning systems may also assist. Post implant CT images may be used, in particular 3-D-based CT planning programs may correlate marker placement. In this manner, bar codes, computer generated location identifiers or, alternatively, US, MR, CT, X-Ray or other image coordinate designations may be used to construct identifier codes for each biopsy specimen. Thus, biopsy histopathology results can be reported to correlate with patient implanted markers which designate by unique marker characteristics the histopathology results for future correlation to unique implanted marker sites which may be used to guide follow-up biopsy and image guided treatments.

Once the biopsy is complete and the fiducial marker or markers in place or otherwise recorded, one will ideally have obtained at least one image of the target tissue which provides an initial data set showing the anatomic volume of the target tissue and a more precisely defined set of target areas within the target tissue defined by the marker images. Depending upon the pathological analysis of the biopsy specimens, these target areas can function as specific biologic target areas for the subsequent application of therapy, or to define a biologic target volume within which therapy can be subsequently directed to the target tissue with, if indicated, variable intensity.

These baseline images are used in combination with additional imagery to provide an ideal data set for defining biological target areas or volumes of occult tumor foci within the target organ or tissue. More specifically, the anatomic images can be co-registered or fused to one or more functional images to compare the functional image-defined tumor area against the specific marker location, such that the target zone may be expanded to include a larger region and/or the positive area identified by biopsy marker can be used to define a focal area for treatment. Alternatively, in the case of a patient with unconfirmed disease (negative biopsy result), but otherwise presenting with strong clinical suspicion for disease (e.g., rising PSA, positive DRE), those sites identified with markers correlating to negative biopsy sites may be utilized with future functional and anatomic images to direct future biopsy at alternative sites.

With the markers in place and/or tracked, one can then obtain any number of subsequent anatomic images, functional images or combinations or hybrids thereof and correlate the information and data provided by those images with the pathology of the target tissue at the marker locations. Advantageously, this is possible whether the subsequent image or pathological data is obtained at the same time or place. Thus, physicians can continue to build an ever more refined picture of the pathology of the target tissue using the definitive pathology defined by the marked biopsy locations as a frame of reference. For example, where an abnormality on a functional image is confirmed to be cancerous based on its correlation with a target area or volume defined by the pathologically confirmed markers, the functional image can then be used to reduce the focal target area, decrease dose intensity or direct therapy to other regions in the target tissue which have not been pathologically confirmed but which show a corresponding abnormality in the functional image suggesting presence of occult tumor foci or volumes. Correlation of the pathology of the marker sites with abnormalities in the functional image can also be used to confirm the accuracy and veracity of the functional image study itself.

To illustrate, a functional image study can be fused to a pelvis image using CAT or MRI and the fiducial markers used to help define a biological target volume for dose intensification. As noted above, current functional studies such as ProstaScint™, SPECT, FDG or C-11 Choline Positron Emission Tomography (PET), and MRI with multiparametric sequences, for example Magnetic Resonance Spectroscopy Imaging (MRSI) often report the suggestion of disease on the image report, however lack adequate sensitivity and specificity to provide confident information to the clinician providing treatment. Further, these image reports fail to define a true BTV as it is impossible to identify where the edge of the tumor is present. By marking and/or tracking the original biopsy locations through anatomic image modalities, the defined sites can be correlated to the volumes showing abnormal signals in the functional image. If the functional study is reported to have high correlations (e.g., tracer uptake pattern, spectroscopy findings) consistent with marker location and histopathology results, the confidence in the functional study to have detected yet occult regions of tumor would be enhanced and may further justify the use of functional studies in treatment planning of, for example, IMRT, brachytherapy, cryotherapy, or other local treatment modalities; or may serve as a surrogate marker for response to therapy in clinical trials.

Suitable image modalities for capturing the marker images will be apparent to those of ordinary skill in the art in view of this disclosure. For example, one can obtain image data sets using any of CT, MR, X-ray, US, Fluoroscopy or a combination or hybrid thereof. Any of the foregoing technologies which are suitable for detecting the markers and creating an anatomic image will provide a useful data set comprising marker location within the target tissue and the corresponding pathology of the tissue at each marker. It is also desired to build on the data set by obtaining functional image data sets (e.g., SPECT, PET, MRSI or a combination or hybrid thereof) and correlating the functional image to the target areas or volumes defined by the marker images. In this way, one can correlate regions of the functional image with the definitive pathology associated with the marker locations and use this data to prescribe and thereafter apply therapy. Thus, it is possible to even further refine diagnosis and treatment using a data set comprised of both anatomic and functional images, or hybrids thereof using commercially available image fusion software, such as Hawkeye Infinia SPECT/CT, Volumetrix Software and Discovery PET/CT from GE Healthcare; Hermes Workstation from Hermes Medical Solutions; AVIA Fusion 7D from Hitachi America Medical Systems; MedView VolumeReg from Medimage; MIM from MIM Vista; Syngo Image Fusion and eSoft Image Fusion from Siemens Medical Solutions; Syntegra GEMNI/Pinnacle3 from Philips Medical Systems; MRSI PROSE Prostate Package software from General Electric Medical Systems; and, IMRT BAT BMode Acquisition and Targeting. Of course, images may be inherently registered when hybrid images are acquired on the same system.

Thus, patients identified as having cancer on positive histopathological findings are most frequently referred for selection of definitive therapy options. Those patients who select, for example, radiation therapy are referred to radiation oncologists for treatment, and those who elect other local therapies are referred to other appropriate oncologists. Alternatively, the diagnosing urologists may treat the patient or the patient may receive treatment from another urologist for such treatment modalities as complete gland excision, high intensity focused ultrasound (HIFU), or cryotherapy. Prior to therapy, patients typically receive anatomic imaging, such as CT, MR or US and, in accordance with the preferred embodiments of the invention, functional imaging such as SPECT, SPECT/CT, PET, PET/CT, SPECT/MRI, multiparametric MRI (mp-MRI) or MRSI or combinations or hybrids thereof, to stage disease and for treatment planning. Once the histopathological and image data are gathered and correlated to provide a useful data set which collectively provide a picture of the pathology of the target tissue, it can then be used to define biological target areas or volumes for purposes of prescribing treatment. Based on the pathology associated with respective markers, as augmented by the functional imaging, one can plan the therapy of the target organ or tissue so as to modulate dose to maximize its effectiveness and minimize harmful side effects or tissue damage. As noted above, to facilitate this analysis it will sometimes be advantageous for the markers themselves to be visually distinguishable from each other on the images or other data sets.

As will be apparent to those of ordinary skill in the art in view of the present disclosure, the process of prescribing therapy comprises the use of the visual data derived from the correlation of the markers and pathology to plan the subsequent treatment. Typically, the gross target volume (GTV) is defined by the anatomic studies with a clinical target volume (CTV) typically comprising the GTV plus an adequate margin to account for microscopic disease at the edge of the GTV and to allow for day-today motion of the GTV from the position at the time of planning, as well as to account for daily error in set up of the patient. Ultrasound or x-ray, for example, are used to see the image visible markers to allow tighter CTV to the GTV by eliminating target motion day to-day and reducing margins to on the order of 4-8 mm. A biological target volume (BTV) typically represents a region defined by a functional study that may be completely within the GTV, or may expand the GTV by showing disease extending beyond the margins defined by the GTV on the anatomic study.

As will be apparent to those of ordinary skill in the art, the visualized markers will assist in defining and refining such biological target areas for purposes of treatment planning and application of therapy. BTV targeting may be achieved manually, by viewing a fiducial marker found to correlate with positive histopathology on one image set and manually applying that information to the treatment planning system (e.g., left lateral apex), such that the treatment dose would be increased to the BTV, or with the aid of treatment planning systems, such as computerized treatment planning software.

An example of computerized treatment planning software utilization in prostate cancer procedures is described in Stone, N. N., et al., Brachytherapy 2(1), March 2003, pp. 17-25, for the registration of radioactive seeds. This procedure can be readily adapted to the instant method making use of the data set generated by the correlation of pathology to marker location Similar to the prostate brachytherapy low dose rate seed implant technique such as that described by Stone et al., which utilizes 5 mm ultrasound slices to reconstruct in three dimensions the dosimetry obtained in the O.R., the location of markers at biopsy positions can be detected by ultrasound, CT scan or MRI and the treatment planning computer can utilize these data sets to assist pre-operatively, intraoperatively or post-operatively in assessment of the therapy plan both prior to and following execution of the plan. These data can then allow utilization of functional BTV volumes to be assessed before, during, and after therapy to assure adequacy of the therapy to treat the individual patient. More specifically, the SPECT/CT, SPECT/MRI and PET/CT, PET/MRI registration process, as well as CT/SPECT/MRSI and CT/PET/MRSI registration, can be made fast and sufficiently accurate to yield a reliable dosimetric analysis using commercially available registration systems, such as MIM from MIM Vista Corp. Since critical normal tissues are often found to reside in dose gradient regions, small shifts in the dose distribution can impact the prediction of complication or complication severity. In the present disclosure, the fiducial markers can be identified, for example, on 2 mm slice CT data set using automatic identification procedures on a reconstructed three-dimensional data set. Marker positions on 3 mm slice thickness T2 MR data sets can be identified using a point-and-click method on each image. Marker images identified on more than one MR slice can be used to determine average marker coordinates for MR images and matched marker pairs between CT and MR images. A least-squares method may be applied to the CT and MR marker coordinates to produce optimum registration. Various commercially available treatment planning systems which can be employed in application of the present method include VariSeed and Eclipse EXT from Varian Medical Systems; KonRad Inverse TPS from Siemens Medical; RAHD 3D/Pro from RAHD Oncology Products; Xplan from Radionics; OptiRad 3D from Permedics; CORVUS from Nomos; PrecisePLAN from Eleckta; ERGO TPS from 3D Line Medical Systems; BrainScan TPS from BrainLab and RTSuite from Multidata Systems.

Advantageously, because the data set used to produce the treatment plan can distinguish and differentiate the specific pathology and tumor progression or aggressiveness of different regions of the target tissue, the treatment plan can be used to direct therapy to different regions of discrete BTV tissue at different intensities.

With the treatment plan in place, one can then proceed to apply therapy to the target BTV in accordance therewith. As will be apparent to those of ordinary skill in the art in view of the instant disclosure, the methods described herein are useful to define a biological target area or volume for the direction and application of any suitable therapy, including IMRT, EBRT, Cryotherapy, LDR, HDR, Hyperthermia, Photo Dynamic Therapy (PDT), Gene Therapy, High Intensity Focused Ultrasound (HIFU) and the like.

Figure 5:
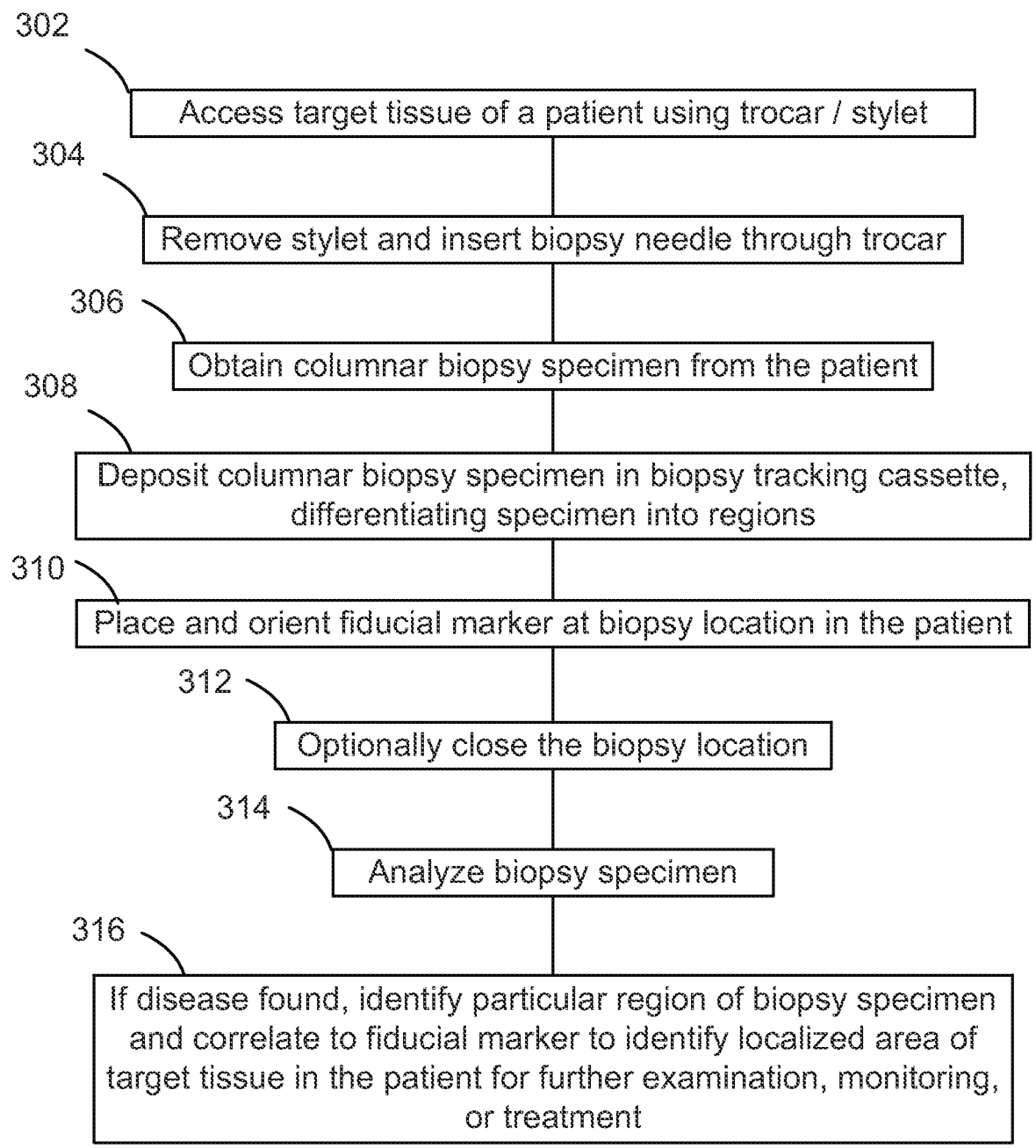
FIG. 5 is a flowchart illustrating one method of using the biopsy kit of the present disclosure and identifying a localized area of target tissue to be treated.

FIG. 5 is a flowchart illustrating some methods of the present disclosure. In step 302, the stylet is inserted into the trocar and used to access the target tissue of the patient at a particular biopsy location. In step 304, the stylet is removed while the trocar is maintained in position, and a biopsy needle is inserted. In step 306, the biopsy needle is used to obtain a columnar biopsy specimen. In step 308, the columnar biopsy specimen is deposited in a biopsy tracking cassette as described above. The biopsy specimen is laid across the coded zones in the tracking cassette, so that the specimen is differentiated into a plurality of regions. In step 310, a fiducial marker is placed at the biopsy location, and is oriented so that a distal end and a proximal end of the fiducial marker correspond to a distal end and a proximal end of the biopsy specimen. In step 312, the biopsy location is sutured or closed. This can be done by inserting a closure needle through the trocar to close the biopsy location, or by removing the trocar and using a separate closure device to close the opening made by the trocar and stylet. In step 314, the biopsy specimen is analyzed. If disease is found in the biopsy specimen, that disease is identified in one or more particular regions of the biopsy specimen that have been coded by the tracking cassette. This permits the particular region(s) of the biopsy specimen to be correlated with orientation of the fiducial marker to identify a localized area in the target tissue to be treated, as indicated by step 316. The localized area is generally smaller than the biopsy specimen, even when margins of error are included, so that treatment can be applied to a smaller area/volume and less healthy tissue is treated.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A method of identifying a localized area of a target tissue of a patient, comprising:
   using a biopsy device to access the target tissue, the biopsy device comprising:
      a trocar having a cannula with a blunt first end and a cupped second end; and
      a stylet having a conical tip at a first end and a cap on a second end, wherein the stylet is inserted into the cannula so that the conical tip extends beyond the blunt first end of the trocar and the cap being sized to engage the cupped second end of the trocar and prevent passage of the second end of the stylet into the cannula;
   removing the stylet from the trocar and inserting a biopsy needle through the trocar;
   obtaining a columnar biopsy specimen from the target tissue at a biopsy location using the biopsy needle, the biopsy specimen having a proximal end and a distal end;
   depositing the columnar biopsy specimen in a biopsy tracking cassette, the biopsy tracking cassette comprising a housing that forms two or more compartments, each compartment having its own lid connected adjacent to a proximal end of the biopsy tracking cassette, and wherein each compartment surface comprises a plurality of coded zones in a single column, the columnar biopsy specimen being deposited to rest across the plurality of coded zones such that the columnar biopsy specimen is differentiated into a plurality of regions;
   placing and orienting at least one fiducial marker substantially at the biopsy location so that the at least one fiducial marker correlates with the proximal end and the distal end of the columnar biopsy specimen;
   analyzing the biopsy specimen to identify a particular region of the biopsy specimen; and
   correlating a location of the particular region of the biopsy specimen with the orientation of the fiducial marker at the biopsy location to identify the localized area of the target tissue.

2. The method of claim 1, further comprising obtaining at least one image of the target tissue to detect a location of the at least one fiducial marker after placing and orienting of the at least one fiducial marker.

3. The method of claim 2, wherein the at least one image is obtained using computed tomography (CT), magnetic resonance imaging (MRI), ultrasound (US), X-ray, fluoroscopy, SPECT, PET, MRSI, optical biopsy, or combinations or hybrids thereof.

4. The method of claim 1, wherein multiple columnar biopsy specimens are obtained from the target tissue at multiple biopsy locations and different fiducial markers are placed and oriented at each biopsy location, the different fiducial markers being distinguishable from each other on an image of the target tissue.

5. The method of claim 4, wherein the different fiducial markers are distinguishable based on their size, shape, image intensity, acoustic impedance, wavelength, or combinations thereof.

6. The method of claim 1, further comprising treating the localized area of the target tissue with an applied therapy.

7. The method of claim 6, wherein the applied therapy is selected from IMRT, EBRT, cryotherapy, LDR, HDR, hyperthermia, photodynamic therapy, HIFU, and gene therapy.

8. The method of claim 1, wherein the coded zones in the biopsy tracking cassette each include a different colored dye to identify different regions on the columnar biopsy specimen.

9. The method of claim 1, further comprising correlating the fiducial marker with the columnar biopsy specimen and the biopsy tracking cassette.

10. The method of claim 1, wherein each compartment comprises an identifier at an end of the internal surface indicating where the distal end of the biopsy specimen is placed.

11. The method of claim 1, wherein the plurality of coded zones in the single column comprises four zones.

12. A biopsy tracking kit, comprising:
   a trocar having a cannula with a blunt first end and a second end with a cup;
   a stylet having a conical tip at a first end and a cap on a second end, the cap being sized to engage the cup of the trocar and prevent passage of the second end of the stylet into the cannula;
   a biopsy needle;
   a biopsy tracking cassette comprising a housing that forms two or more compartments, each compartment having its own lid connected adjacent to a proximal end of the biopsy tracking cassette, and each compartment having an internal surface with a plurality of coded zones in a single column; and
   at least one fiducial marker which can be distinguished on an image.

13. The biopsy tracking kit of claim 12, wherein the cup of the trocar is in the shape of a cone, and is adapted to receive the conical tip of the stylet.

14. The biopsy tracking kit of claim 12, wherein the conical tip of the stylet extends at least 0.5 cm beyond the blunt first end of the trocar when fully inserted through the trocar.

15. The biopsy tracking kit of claim 12, wherein the cap of the stylet is in the shape of a right conical frustum.

16. The biopsy tracking kit of claim 12, wherein the internal surface of the biopsy tracking cassette is a mesh, and the plurality of coded zones is arranged in a single column from a distal end of the internal surface to a proximal end of the internal surface.

17. The biopsy tracking kit of claim 12, wherein the biopsy tracking cassette further comprises a housing for the internal surface.

18. The biopsy tracking kit of claim 17, wherein the housing and the lid of the biopsy tracking cassette are formed as a single piece.

19. The biopsy tracking kit of claim 17, wherein the housing and the lid of the biopsy tracking cassette include pores.

20. The biopsy tracking kit of claim 12, wherein the fiducial marker has a length that is from about 15 mm to about 25 mm.

21. The biopsy tracking kit of claim 12, wherein the fiducial marker has spaced apart markings that are visually distinguishable on an image.

22. A biopsy tracking cassette comprising a housing that forms two or more compartments, each compartment having its own lid connected adjacent to a proximal end of the biopsy tracking cassette, and each compartment containing an internal surface with a plurality of coded zones arranged in a single column from a distal end of the internal surface to a proximal end of the internal surface.

\* \* \* \* \*